United States Patent
Paukshto et al.

(10) Patent No.: US 9,724,308 B2
(45) Date of Patent: Aug. 8, 2017

(54) BIODEGRADABLE MULTILAYER CONSTRUCTS

(75) Inventors: Michael V. Paukshto, Foster City, CA (US); George R. Martin, Rockville, MD (US); David H. McMurtry, Felton, CA (US)

(73) Assignee: Fibralign Corporation, Union City, CA (US)

(*) Notice: Subject to any disclaimer, the term of this patent is extended or adjusted under 35 U.S.C. 154(b) by 872 days.

(21) Appl. No.: 13/821,530

(22) PCT Filed: Sep. 10, 2011

(86) PCT No.: PCT/US2011/051135
§ 371 (c)(1),
(2), (4) Date: Aug. 30, 2013

(87) PCT Pub. No.: WO2012/034110
PCT Pub. Date: Mar. 15, 2012

(65) Prior Publication Data
US 2014/0081070 A1    Mar. 20, 2014

Related U.S. Application Data

(60) Provisional application No. 61/403,006, filed on Sep. 10, 2010.

(51) Int. Cl.
*A61N 2/00* (2006.01)
*A61K 9/70* (2006.01)
(Continued)

(52) U.S. Cl.
CPC .......... *A61K 9/70* (2013.01); *A61F 13/00063* (2013.01); *A61L 27/04* (2013.01);
(Continued)

(58) Field of Classification Search
CPC .. A61L 27/3683; A61L 27/3687; A61L 31/12; A61L 2400/12; A61L 27/24;
(Continued)

(56) References Cited

U.S. PATENT DOCUMENTS 4,060,081 A    11/1977  Yannas et al.
4,478,630 A    10/1984  Lambert
(Continued)

FOREIGN PATENT DOCUMENTS

EP    0 518 697 A2    12/1992
JP    2004-148014 A    5/2004
(Continued)

OTHER PUBLICATIONS

Besseau, L. et al., "Production of Ordered Collagen Matrices for Three-Dimensional Cell Culture," Biomaterials, 23, 2002, pp. 27-36.
(Continued)

*Primary Examiner* — Samuel Gilbert
(74) *Attorney, Agent, or Firm* — Nixon Peabody LLP

(57) ABSTRACT

Embodiments of the present invention relate generally to the field of tissue repair and regeneration. More specifically embodiments of present disclosure relate to devices or constructs and methods to prepare various devices or constructs useful in directing cellular repair and controlling tissue regeneration to prevent or minimize postsurgical or post traumatic adhesions, excessive scars and/or fibrotic reactions of injured tissues.

24 Claims, 9 Drawing Sheets

(51) Int. Cl.

| | | |
|---|---|---|
| *A61L 27/04* | (2006.01) | |
| *A61L 27/20* | (2006.01) | |
| *A61L 27/24* | (2006.01) | |
| *A61L 27/54* | (2006.01) | |
| *A61L 27/56* | (2006.01) | |
| *A61F 13/00* | (2006.01) | |
| *A61M 35/00* | (2006.01) | |

(52) U.S. Cl.
CPC .............. *A61L 27/20* (2013.01); *A61L 27/24* (2013.01); *A61L 27/54* (2013.01); *A61L 27/56* (2013.01); *A61M 35/00* (2013.01); *A61N 2/002* (2013.01); *A61L 2400/12* (2013.01); *A61L 2420/08* (2013.01); *A61L 2430/38* (2013.01)

(58) Field of Classification Search
CPC ........... A61L 27/54; A61F 2310/00982; A61F 2310/00371
USPC .................................................. 600/9–15, 37
See application file for complete search history.

(56) References Cited

U.S. PATENT DOCUMENTS

| | | |
|---|---|---|
| 4,544,516 A | 10/1985 | Hughes et al. |
| 4,759,354 A | 7/1988 | Quarfoot |
| 4,869,200 A | 9/1989 | Euverard |
| 4,902,508 A | 2/1990 | Badylak et al. |
| 5,171,273 A | 12/1992 | Silver et al. |
| 5,744,545 A | 4/1998 | Rhee et al. |
| 5,922,028 A | 7/1999 | Plouhar et al. |
| 6,087,549 A | 7/2000 | Flick |
| 6,544,762 B1 | 4/2003 | Tranquillo et al. |
| 6,592,623 B1 | 7/2003 | Bowlin et al. |
| 6,737,053 B1 | 5/2004 | Goh et al. |
| 6,824,716 B2 | 11/2004 | Liao et al. |
| 6,861,570 B1 | 3/2005 | Flick |
| 6,887,488 B2 | 5/2005 | Cui et al. |
| 7,048,963 B2 | 5/2006 | Braithwaite et al. |
| 7,214,847 B1 | 5/2007 | Flick |
| 7,230,153 B2 | 6/2007 | Flick |
| 7,338,517 B2 | 3/2008 | Yost et al. |
| 7,354,627 B2 | 4/2008 | Pedrozo et al. |
| 7,596,415 B2 | 9/2009 | Brabec |
| 7,890,179 B2 | 2/2011 | Wiegmann et al. |
| 7,908,016 B2 | 3/2011 | Atanasoska et al. |
| 8,028,647 B2 | 10/2011 | McMurtry |
| 8,118,791 B2 | 2/2012 | Flick et al. |
| 8,449,514 B2 | 5/2013 | Flick |
| 8,513,382 B2 | 8/2013 | Paukshto et al. |
| 2003/0093107 A1 | 5/2003 | Parsonage et al. |
| 2003/0139806 A1 | 7/2003 | Haverkost et al. |
| 2003/0153965 A1 | 8/2003 | Supronowicz et al. |
| 2003/0176827 A1 | 9/2003 | Chandra et al. |
| 2005/0009178 A1 | 1/2005 | Yost et al. |
| 2005/0019488 A1 | 1/2005 | Braithwaite et al. |
| 2005/0038498 A1 | 2/2005 | Dubrow et al. |
| 2005/0240261 A1 | 10/2005 | Rakos et al. |
| 2005/0267231 A1 | 12/2005 | Pavlin |
| 2006/0141015 A1 | 6/2006 | Tessier et al. |
| 2006/0198827 A1 | 9/2006 | Levenberg |
| 2007/0041952 A1 | 2/2007 | Guilak et al. |
| 2007/0123766 A1 | 5/2007 | Whalen, III et al. |
| 2007/0207186 A1 | 9/2007 | Scanlon et al. |
| 2007/0244569 A1 | 10/2007 | Weber et al. |
| 2008/0115724 A1 | 5/2008 | McMurtry et al. |
| 2008/0125687 A1 | 5/2008 | Flick et al. |
| 2008/0147199 A1 | 6/2008 | Yost et al. |
| 2008/0254091 A1 | 10/2008 | Lee et al. |
| 2008/0286447 A1 | 11/2008 | Alden et al. |
| 2008/0306580 A1* | 12/2008 | Jenson ...................... A61F 2/07 623/1.11 |
| 2009/0069893 A1* | 3/2009 | Paukshto ................ A61L 27/24 623/13.11 |
| 2009/0117087 A1 | 5/2009 | Carroll et al. |
| 2009/0117807 A1 | 5/2009 | Uno et al. |
| 2009/0124956 A1 | 5/2009 | Swetlin et al. |
| 2009/0163936 A1* | 6/2009 | Yang ...................... A61L 27/20 606/151 |
| 2009/0252861 A1 | 10/2009 | Tessier et al. |
| 2009/0264718 A1* | 10/2009 | Lesho ................... A61B 5/0031 600/310 |
| 2009/0297581 A1 | 12/2009 | Atanasoska et al. |
| 2010/0016872 A1* | 1/2010 | Bayon ................... A61F 2/0063 606/151 |
| 2010/0036098 A1 | 2/2010 | Paukshto et al. |
| 2010/0106233 A1 | 4/2010 | Grant et al. |
| 2011/0151563 A1 | 6/2011 | Paukshto et al. |
| 2011/0217544 A1 | 9/2011 | Young et al. |
| 2012/0065703 A1 | 3/2012 | Paukshto et al. |
| 2013/0287744 A1 | 10/2013 | Paukshto et al. |

FOREIGN PATENT DOCUMENTS

| | | |
|---|---|---|
| JP | 07-213597 | 8/2007 |
| JP | 2008-504921 | 2/2008 |
| JP | 09-122227 | 6/2009 |
| WO | WO 84/00548 A1 | 2/1984 |
| WO | WO 99/47188 A1 | 9/1999 |
| WO | WO 00/61045 A1 | 10/2000 |
| WO | WO 03/020316 A1 | 3/2003 |
| WO | WO 2004/050134 A2 | 6/2004 |
| WO | WO 2005/003300 A2 | 1/2005 |
| WO | WO 2005/081699 A2 | 9/2005 |
| WO | WO 2006/136817 A1 | 12/2006 |
| WO | WO 2007/028078 A2 | 3/2007 |
| WO | WO 2007/038601 A2 | 4/2007 |
| WO | WO 2008/034854 A1 | 3/2008 |
| WO | WO 2008/063631 | 5/2008 |
| WO | 2008-070166 A1 * | 6/2008 ............. A61L 27/14 |
| WO | WO 2008/070166 A1 | 6/2008 |
| WO | WO 2008/131293 | 10/2008 |
| WO | WO 2009/064437 A1 | 5/2009 |
| WO | WO 2010/019625 A2 | 2/2010 |
| WO | WO 2010/022353 A1 | 2/2010 |
| WO | WO 2012/034110 | 3/2012 |

OTHER PUBLICATIONS

Bobrov, Y, et al., "The manufacture of a thin film LCD", Journal of the SID, Oct. 4, 2002, pp. 317-321.
Chen, J. et al., "Scaffolds for tendon and ligament repair: review of the efficacy of commercial products", Expert Reviews Ltd., 2009, 6(1), pp. 61-73.
Cisneros, D. et al., "Creating Ultrathin Nanoscopic Collagen Matrices for Biological and Biotechnological Applications", Wiley InterScience, 2007, vol. 3, No. 6, pp. 956-963.
Cornwell, K., et al., "Crosslinking of discrete self-assembled collagen threads: effects on mechanical strength and cell-matrix interactions", Journal of Biomedical Materials Research Part A., 2007, 80A, pp. 362-371.
Cowin, S., "Do Liquid Crystal-Like Flow Processes Occur in the Supramolecular Assembly of Biological Tissues?", J. Non-Newtonian Fluid Mech. 119, 2004, pp. 155-162.
Enea, D. et al., "Extruded collagen fibres for tissue engineering applications: effect of crosslinking method on mechanical and biological properties", J. Mater. Sci: Mater. Med., 2011, 22, pp. 1569-1578.
Eglin, D. et al., "Type I Collagen, a Versatile Liquid Crystal Biological Template for Silica Structuration from Nano-to Microscopic Scales," The Royal Society of Chemistry, vol. 1, 2005, pp. 129-131.
European Examination Report in Application No. EP 08746355.0, dated Mar. 31, 2011.
European Examination Report in Application No. EP 08746355.0, dated Sep. 5, 2011.
European Search Report and Opinion from European Application No. EP 08746355.0, dated Jun. 4, 2010, 8 pages.

(56) References Cited

OTHER PUBLICATIONS

Evans, H., et al. "Novel 3D Culture System for Study of Cardiac Myocyte Development," Am J. Physiol Heart Circ Physiol, vol. 285, 2003, pp. H570-H578.
Fennell, L. et al., "Thin Crystal Film Polarizers," Asia Display/IDW, 2001, pp. 601-603.
Freed, A.D. et al., "Elastic Model for Crimped Collagen Fibril, "Journal of Biomechanical Engineering, Aug. 2005, vol. 127, pp. 587-593.
Gobeaux, F., "Cooperative Ordering of Collagen Triple Helices in the Dense State", Langmuir 2007, vol. 23, pp. 6411-6417.
Guo, C. et al., "Flow and'Magnetic Field Induced Collagen Alignment," Biomaterials, vol. 28, 2007, pp. 1105-1114.
Hansen, U. et al., "Material Properties of Biological Tissues Related to Joint Surgery," Current Orthopaedics, vol. 20, 2006, pp. 16-22.
International Search Report and Written Opinion in PCT/US2008/060919, dated Oct. 17, 2008.
International Search Report and Written Opinion in PCT/US2007/025037, dated Apr. 8, 2008.
International Search Report and Written Opinion in PCT/US2011/051135, dated Apr. 26, 2012.
International Search Report and Written Opinion in PCT/US2009/053486, dated Mar. 26, 2010.
Kirkwood, J.E., et al., "Liquid Crystalline Collagen: A Self-Assembled Morphology for the Orientation of Mammalian Cells", Langmuir, 2009, vol. 25, No. 5, pp. 3200-3206.
Knight, D. et al. "Biological Liquid Crystal Elastomers," Philosophical Transactions: Biological Sciences, vol. 357, No. 1418, Estomeric Proteins: Structures, Biomechanical Properties and Biological Roles., Feb. 12, 2002, pp. 155-163.
Ledet, E. H. et al., "A Pilot Study to Evaluate the Effectiveness of Small Intestinal Submucosa Used to Repair Spinal Ligaments in the Goat," The Spine Journal, vol. 2, No. 3, May-Jun. 2002, pp. 188-196.
Martin, G. R. et al., "Behavior Of Cells On Highly Organized and Reconstituted Collagen Matices," The Cell, Bethesda MS USA, vol. 19, Dec. 13, 2008, p. 42.
Martin, R. et al., "Liquid Crystalline Ordering of Procollagen as a Determinant of Three-Dimensional Extracellular Matrix Architecture," J. Mol. Biol., vol. 301, 2000, pp. 11-17.
Mosser, G., et al., "Dense tissue-like collagen matrices formed in cell-free conditions", Matrix Biology, 2006, 25, pp. 3-13.
McPherson, T.B. et al., "Characterization of Fibronectin Derived from Porcine Small Intestinal Submucosa," Tissue Engineering, vol. 4, No. 1, 1998, pp. 75-83.
Muthusubramaniam, L. et al., "Collagen Fibril diameter and alignment promote the quiescent keratocyte phenotype", Journal of Biomedical Materials Research A, Mar. 2012, vol. 100A, Issue 3, pp. 613-621.
Ng, C. P. et al., "Fibroblast Alignment Under Interstitial Fluid Flow Using a Novel 3-D Tissue Culture Model," Am J. Physical Heart Circ. Physiol, vol. 284, Jan. 16, 2003, pp. H1771-H1777.
Notice of Allowance in U.S. Appl. No. 11/951,324, mailed Mar. 20, 2012.
Notice of Allowance in U.S. Appl. No. 12/106,214, mailed Jul. 2, 2012.
Office Action in U.S. Appl. No. 11/951,324, mailed Sep. 7, 2011.
Office Action in U.S. Appl. No. 12/106,214, mailed Aug. 5, 2011.
Office Action in U.S. Appl. No. 12/106,214, mailed Jan. 19, 2012.
Paukshto, M. et al., "Optics of Sheared Liquid-Crystal Polarizer Based on Aqueous Dispersion of Dichroic-Dye Nano-Aggregates", Journal of the SID, 13/9, 2005, pp. 765-772.
Tan, W. et al. "Layer-by-Layer Microfluidics for Biomimetic Three-Dimensional Structures," Biomaterials, 2004, vol. 25, pp. 1355-1364.
Yoshizato, K. et al., "In Vitro Orientation of Fibroblasts and Myoblasts on Aligned Collagen Film," Develop., Growth and Differ., 23 (2), 1981, pp. 175-184.

Zeugolis, D. et al., "Cross-linking of extruded collagen fibers—A biomimetic three-dimensional scaffold for tissue engineering applications", Journal of Biomedical Materials Research A, 2009, 89A, pp. 895-908.
Zhong, S. et al., "An Aligned Nanofibrous Collagen Scaffold by Electrospinning and its Effects on In Vitro Fibroblast Culture," Journal of Biomedical Materials Research Part A, 2006 Wiley Periodicals, Inc., pp. 456-463.
Office Action in U.S. Appl. No. 12/539,563, mailed Jun. 7, 2012.
Office Action in U.S. Appl. No. 12/539,563, mailed Jan. 25, 2013.
Notice of Allowance in U.S. Appl. No. 12/539,563, mailed Apr. 17, 2013.
Supplemental Notice of Allowability in U.S. Appl. No. 12/539,563, mailed Jul. 2, 2013.
Freed, A.D. et al., "Elastic Model for Crimped Collagen Fibril," Journal of Biomechanical Engineering, Aug. 2005, vol. 127, pp. 587-593.
Jiang, et al., Assembly of collagen into microribbons: effects of pH and electrolytes; Journal of Structural Biology, Academic Press, United States, vol. 148, No. 3, Dec. 1, 2004; pp. 268-278.
Kim et al., "Antimicrobial effect of silver-impregnated cellulose: potential for antimicrobial therapy", Journal of Biological Engineering, 3:Dec. 20, 2009, 9 pgs.
Koster, et al., Visualization of Flow-Aligned Type I Collagen Self-Assembly in Tunable pH Gradients; Langmuir, vol. 23, 2007, pp. 357-359.
Wijnhoven, S. W.P. et al., "Nano-Silver—a Review of Available Data and Knowledge Gaps in Human and Environmental Risk Assessment," Nonotoxicology, Jun. 2009, 3(2), pp. 109-138.
Wikipedia, "Units of textile measurement", Downloaded from <http://en.wikipedia.org/wiki/Units_of_textile_measurement> on Feb. 13, 2015; 5 pages.
Australian Examination Report No. 1 in Application No. AU 2009282095 dated Mar. 7, 2014.
Australian Examination Report No. 2 in Application No. AU 2009282095 dated Mar. 16, 2015.
European Examination Report for European Application No. EP 09807197 dated May 26, 2014, 5 pages.
European Extended Search Report and Opinion for European Application No. EP 09807197, dated Jul. 10, 2013, 10 pages.
European Extended Search Report and Opinion for European Application No. EP 11824229.6, dated Jul. 17, 2014, 8 pages.
International Preliminary Report on Patentability in PCT/US2009/053486 mailed Feb. 15, 2011; 5 pages.
International Preliminary Report on Patentability in PCT/US2011/051135 dated Mar. 12, 2013.
International Search Report and Written Opinion in PCT/US2009/053486 mailed Mar. 26, 2010.
International Search Report and Written Opinion in PCT/US2011/044231 mailed Mar. 20, 2012.
Japanese Patent Application No. 2011-523126 Office Action dated Sep. 29, 2015.
Office Action in U.S. Appl. No. 12/539,563 mailed Dec. 1, 2011.
Office Action in U.S. Appl. No. 13/184,313 mailed Jun. 22, 2016.
Office Action in U.S. Appl. No. 13/184,313 mailed Feb. 24, 2015.
Office Action in U.S. Appl. No. 13/184,313 mailed Jan. 13, 2014.
Office Action in U.S. Appl. No. 13/184,313 mailed Jun. 10, 2013.
Office Action in U.S. Appl. No. 13/184,313 mailed May 6, 2015.
Office Action in U.S. Appl. No. 13/184,313 mailed Sep. 12, 2013.
Office Action in U.S. Appl. No. 13/184,313 mailed Nov. 9, 2015.
Office Action in U.S. Appl. No. 13/925,005 mailed Aug. 16, 2016.
Office Action in U.S. Appl. No. 13/925,005 mailed Aug. 27, 2015.
Office Action in U.S. Appl. No. 13/925,005 mailed Nov. 5, 2015.
Del Bianco, S. et al., "Effect of a clear layer at the surface of a diffusive medium on measurements of transmittance and reflectance", Optics Express, vol. 12, No. 22, Nov. 2004, pp. 5510-5517.
Hu, L. et al., "Scalable Coating and Properties of Transparent, Flexible, Silver Nanowire Electrodes", ACS Nano, vol. 4, No. 5, Apr. 2010 (online), pp. 2955-2963.

* cited by examiner

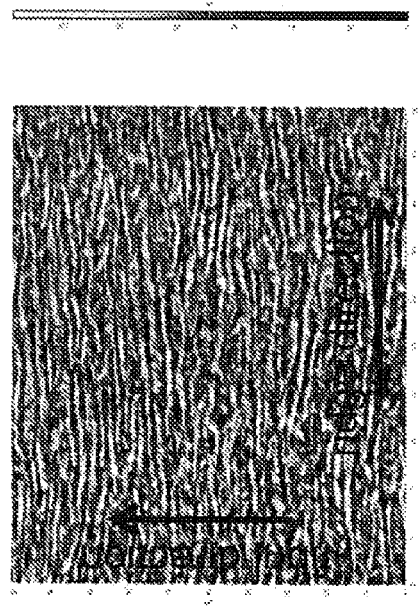
FIG. 1A. Cornea-like
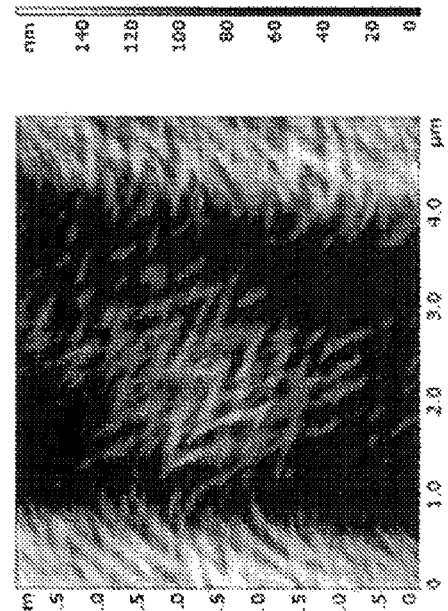
FIG. 1B. Tendon-like
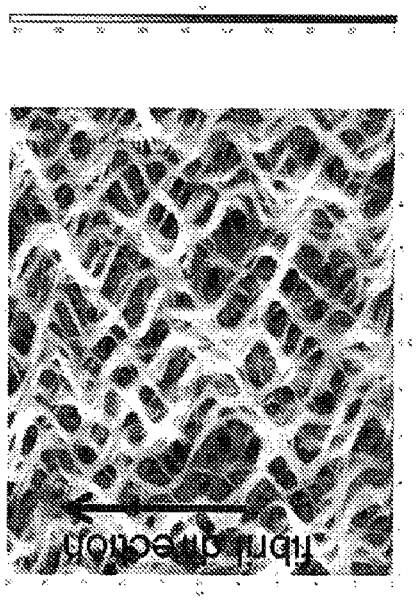
FIG. 1C. Skin-like
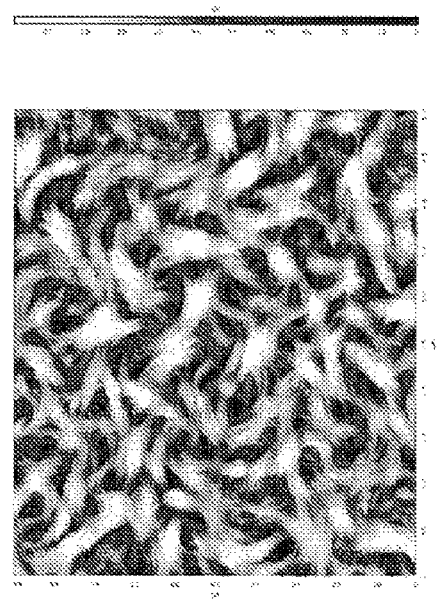
FIG. 1D. Basket-Weave

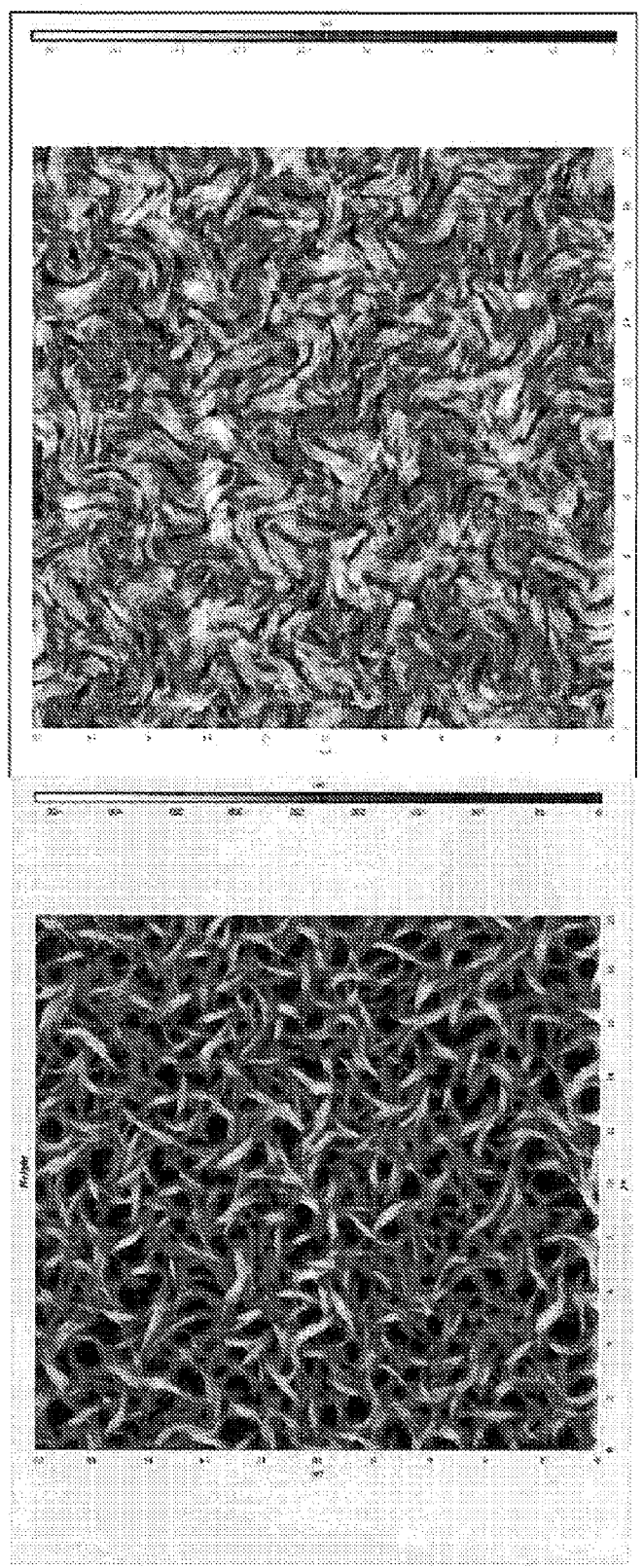
FIG. 2B Skin-like water-tight membrane
FIG. 2A Skin-like porous membrane

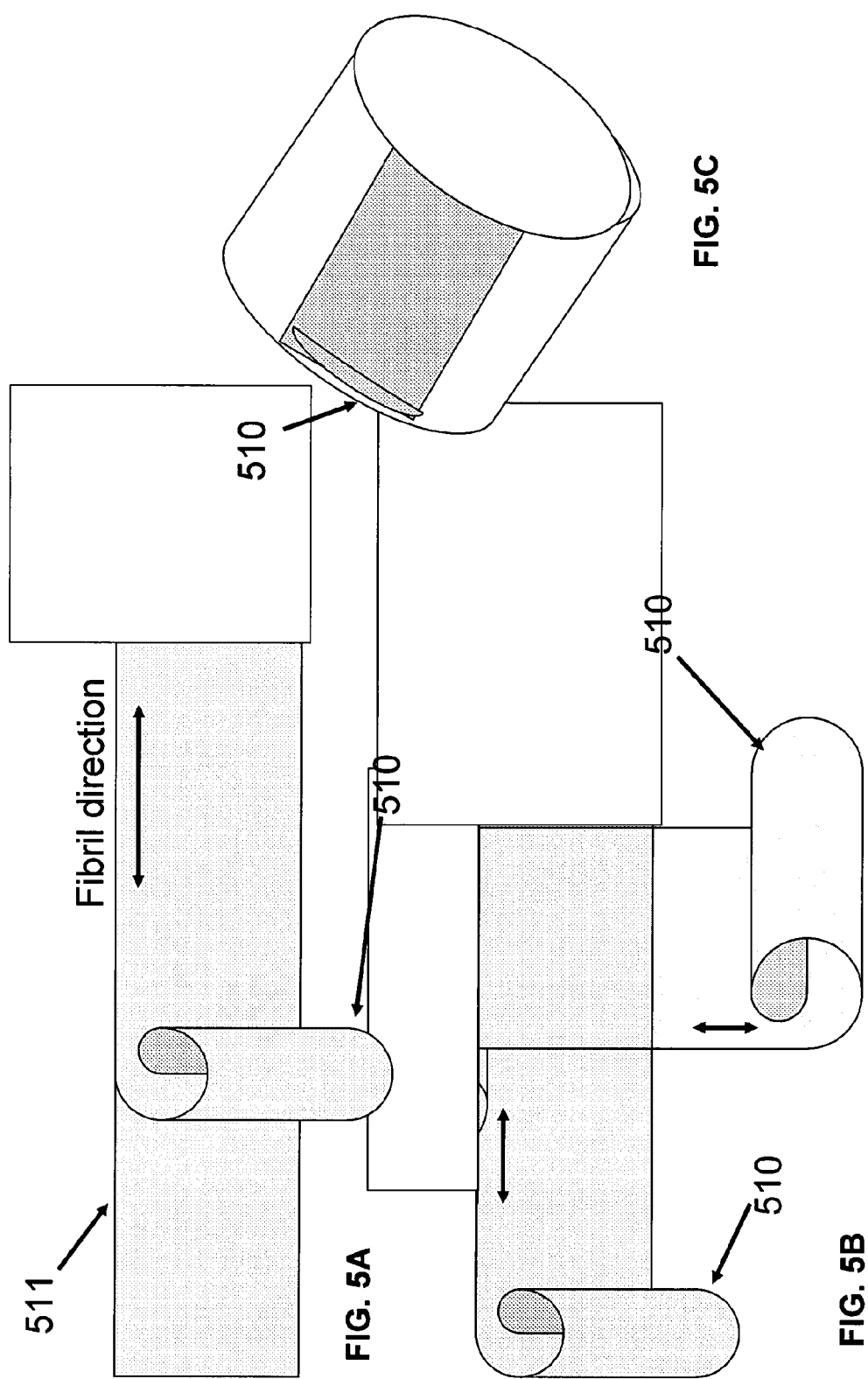

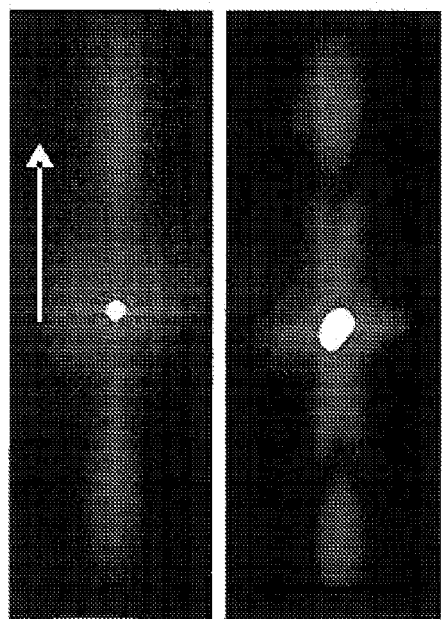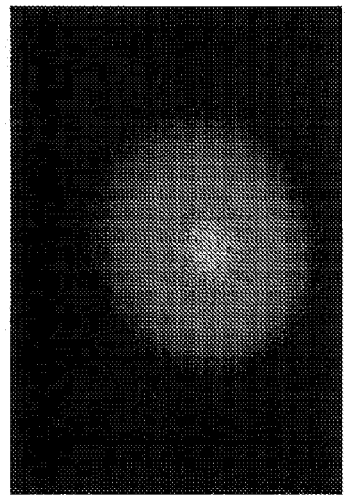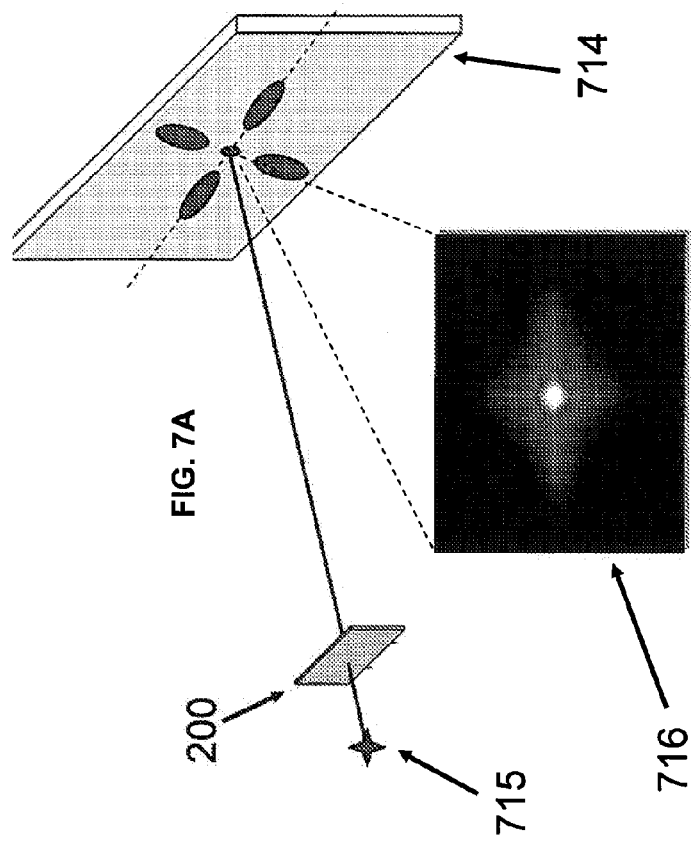

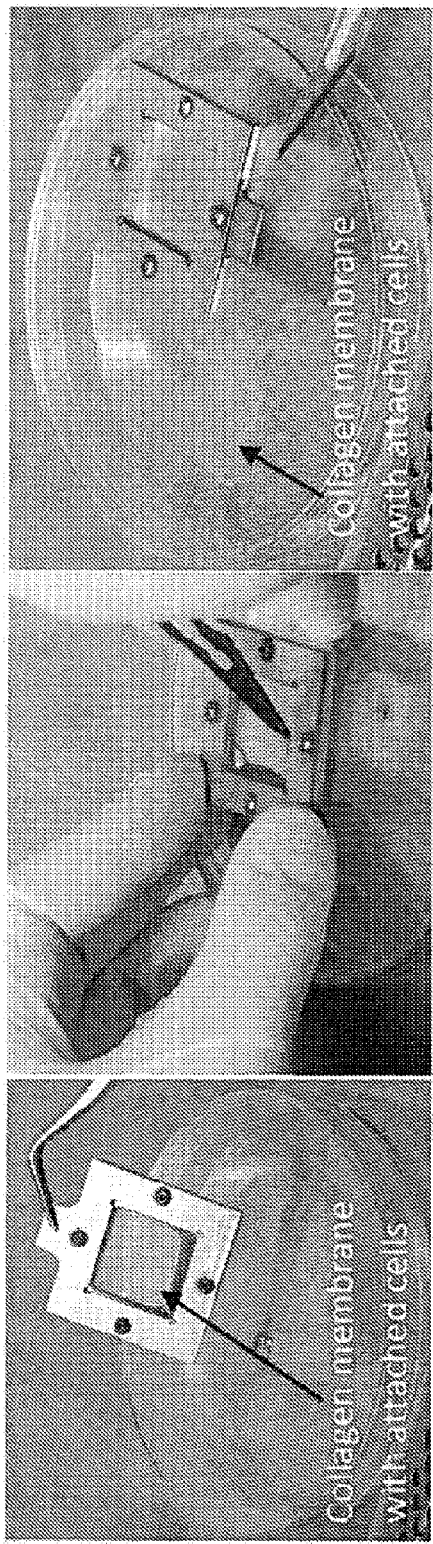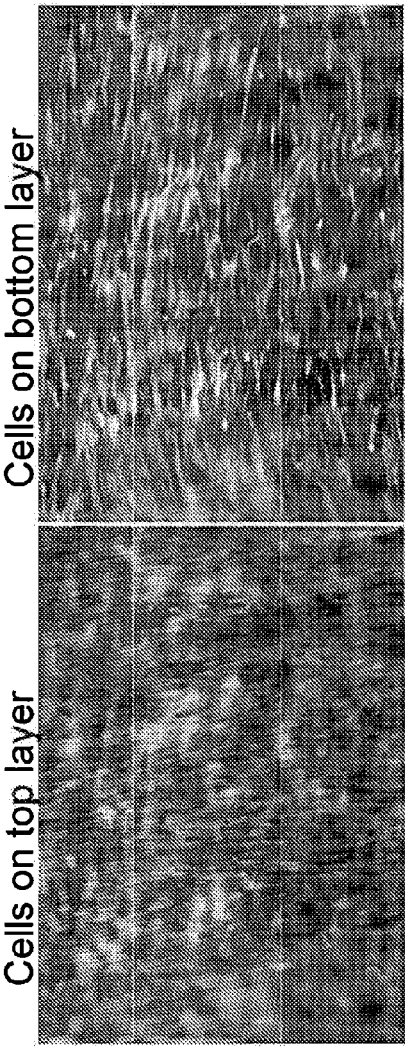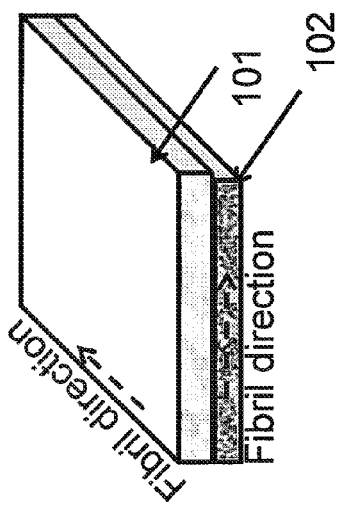
FIG. 9A
FIG. 9B
FIG. 9C

BIODEGRADABLE MULTILAYER CONSTRUCTS

CROSS REFERENCE TO RELATED APPLICATIONS

This patent application is a United States National Stage Application filed under 35 U.S.C. §371 of International Application No. PCT/US2011/051135 entitled "Biodegradable Multilayer Constructs" which was filed on Sep. 10, 2011 which claims the benefit of, and priority to, U.S. Provisional Patent application Ser. No. 61/403,006 filed on Sep. 10, 2010, the entire disclosure of which is hereby incorporated by reference.

TECHNICAL FIELD

Embodiments of the present invention relate generally to the field of tissue repair and regeneration. More specifically embodiments of present disclosure relate to devices or constructs and methods to prepare various devices or constructs useful in directing cellular repair and controlling tissue regeneration to prevent or minimize postsurgical or post-traumatic adhesions, excessive scars and/or fibrotic reactions of injured tissues.

BACKGROUND OF THE INVENTION

Adhesions form as a natural part of the body's healing process after surgery or trauma in a process similar to the way that a scar forms. The term "adhesion" is typically used when the scar extends from one tissue to another, linking the two. In response to injury and bleeding the body deposits fibrin onto injured tissues. The fibrin acts like a glue to seal the injury and is the initial glue that builds the fledgling adhesion, generally referred at this point to be "fibrinous." In body cavities such as the peritoneal, pericardial and synovial cavities, a family of fibrinolytic enzymes may act to limit the extent of the fibrinous adhesion, and may even dissolve it. In many cases however, the production or activity of these enzymes are compromised because of injury, and the fibrinous adhesion persists. If this is allowed to happen, tissue repair cells such as macrophages, fibroblasts and blood vessel cells, penetrate into the fibrinous adhesion, and unguided by a proper matrix lay down collagen and other matrix substances to form a permanent fibrous adhesion.

While some adhesions do not cause problems, others can prevent tissues and organs from moving freely, sometimes causing organs to become twisted or pulled from their normal positions. The sequence of adhesion formation is believed to occur and has been reported as follows: tissue ischemia, inflammation, fibrin deposition, fibrin organization, collagen formation, and maturation with the formation of adhesions. Surgeons use several agents to reduce adhesion formation at each of these steps. Physical barriers, including both mechanical and viscous solutions, are widely used to prevent adhesion formation by limiting and guiding tissue apposition during the critical stages of mesothelial repair. However, at least 50% of patients still develop significant adhesions. Moreover, there is no satisfactory way to monitor non-invasively the formation of unwanted adhesions after application of these techniques to a patient. Thus, improvements and further developments are critically needed.

Purified collagen from animals or humans is widely used in various medical devices, in research, and in cosmetics. However, the materials prepared from soluble purified collagen lack the macrostructure and organization seen in tissues. For example, the collagen fibers in tendon are highly aligned for maximal tensile strength, but also have a kinked structure to allow some give to the tissue. In contrast, the collagen in the cornea is arranged as small parallel transparent fibers. The collagen in the skin is arranged in bundles, not parallel, which allows more expansion and flexibility than seen with tendon. Each structure has obvious advantages to the tissue it comprises. Each structure is unique.

Collagen prepared from both human and animal sources has been shown to be safe and of minimal immunogenicity when implanted into humans. Collagen has the advantages that it is biocompatible, can form structures with high tensile strength, that the tensile strength of the constructs can be increased by covalent cross-linking and that the construct is replaced by normal tissue by repair and regeneration.

Methods to deposit collagen molecules in defined structures including aligned, woven and transparent materials convertible into bandages, sutures and multilayered structures for diverse indications are described in U.S. patent application Ser. Nos. 11/951,324, 11/986,263, 12/106,214, and 12/539,563, all of which are incorporated by reference herein in their entirety. One advantage of these collagen materials is that they closely approximate the natural structures of tissues, are biocompatible and induce the guided growth of cells attaching to them. The collagen materials appear to be an excellent substrate for applying mesenchymal and other stem cells to precise tissue sites. While these advances have been made, there is significant need for continued advancement and development of devices, constructs, implants and methods that promote and/or enhance tissue repair and regeneration, particularly constructs that provide an anti-adhesion barrier.

SUMMARY OF THE INVENTION

Accordingly, some embodiments of the present disclosure provide medical devices, materials or constructs and methods that enhance and/or promote tissue repair and regeneration. In some aspects, embodiments of present disclosure relate to devices and methods to prepare various constructs from soluble collagen and other material, either alone or in combination, to direct cellular repair and control tissue regeneration to prevent postsurgical or post-traumatic adhesions, excessive scars and fibrotic reactions of injured tissues. Certain embodiments enable the constructs to be monitored in situ when implanted.

In one aspect, a method is provided comprising the steps of preparing a biopolymer based multilayer construct, covering and separating tissue using this construct and inducing repair and regeneration of a defect or injury. In some embodiments a material or construct is provided comprised of: a composition of at least one biocompatible polymer (also referred to as "biopolymer") and one or more metal nanowires. A medical device is also described, comprising: at least one connected network of metal nanowires and at least one biocompatible polymer, and wherein the device exhibits electric conductivity in at least one direction across the device, and at least some of the network of metal nanowires are disposed in at least part of the biocompatible polymer. In some embodiments, the metal nanowires are at least partially aligned in at least one direction.

Each collagen rich tissue, i.e. cornea, tendon, skin and bone, has a unique arrangement of collagen fibers compatible with tissue requirements. The ability to duplicate these structures using purified collagen according to the present invention offers new opportunities to bridge damage, to deliver cells to specific sites and to incorporate factors into the materials which aid repair. Embodiments of the present invention provide novel constructs prepared from collagenous materials reconstituted from soluble collagen to prevent or minimize post surgical or post-traumatic adhesion, and to reduce scar formation and fibrotic reaction on the injured surface of a mammal tissue. Of significant advantage, the inventive constructs more closely replicate the structures of various normal tissue and influence non-scarring cell phenotype.

BRIEF DESCRIPTION OF THE FIGURES

The foregoing and other aspects of embodiments of the present disclosure will be apparent upon consideration of the following detailed description, taken in conjunction with the accompanying drawings, in which like reference characters refer to like parts throughout, and in which:

FIGS. 1A-1D are four atomic force microscopy (AFM) images of different nanoweave collagen layers or membranes reconstituted from purified monomeric collagen solution in accordance with U.S. patent application Ser. Nos. 11/951,324, 11/986,263, 12/106,214, and 12/539,563 and used in embodiments of the present disclosure;

FIGS. 2A-2B are AFM images of two different nanoweave collagen layers or membranes reconstituted from purified monomeric collagen solution according to U.S. patent application Ser. Nos. 11/951,324, 11/986,263, 12/106,214, and 12/539,563 and having different porosity according to embodiments of the present disclosure;

FIGS. 5A-5C are an illustration showing an exemplary method of preparing a multilayer construct according to embodiments of the present disclosure;

FIGS. 7A-7C show unique diffraction patterns of multilayer constructs made according to embodiments of the present disclosure, as compared to a typical collagen layer or membrane which shows no orientation as seen in FIG. 7C;

FIGS. 9A-9C are a series of photographs and drawing illustrating the use of a multilayer collagen construct (FIG. 9B) with orthogonal orientation of fibrils. As shown in FIG. 9C, two different cell types are plated on the top and bottom sides of the construct (e.g., epithelial and endothelial cells in the case of corneal in-vitro model or smooth muscle and endothelial cells in the case of blood vessel in-vitro model). The construct with the attached cells can be further transferred into specific animal site (e.g., to a wound or to another in-vitro system as shown at the FIG. 9A.).

DETAILED DESCRIPTION OF THE INVENTION

Figure 3:
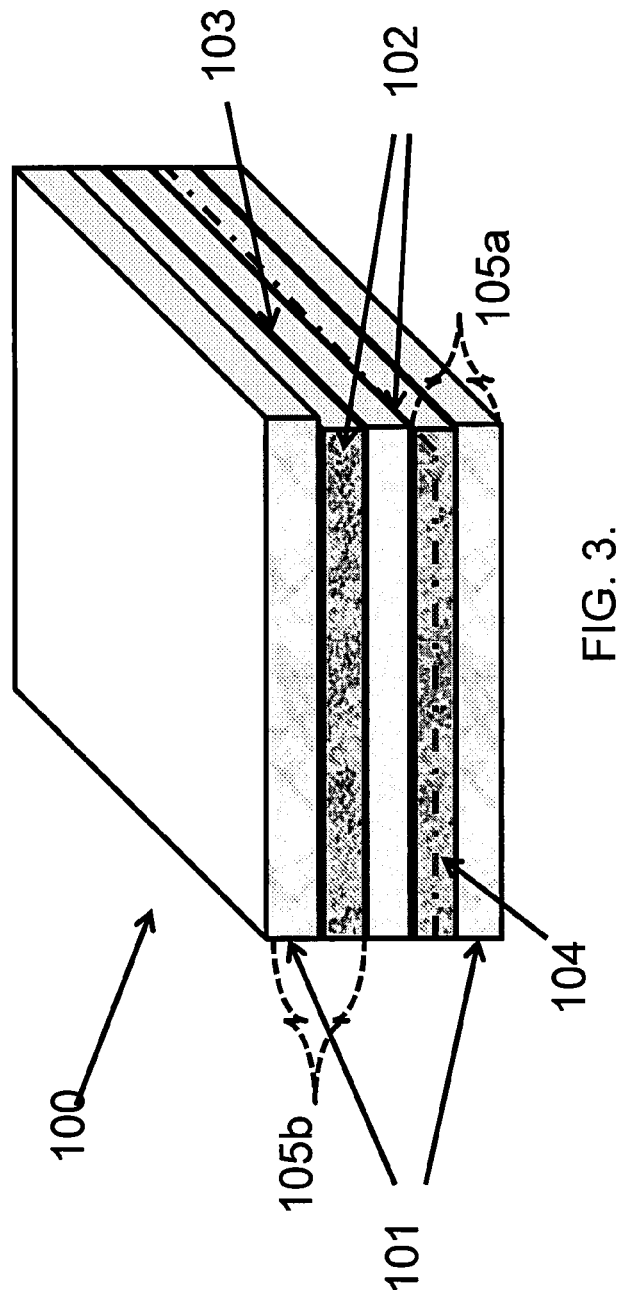
FIG. 3 is a schematic diagram of a biopolymer device or construct having multiple layers according to embodiments of the present disclosure.

It is to be understood that both the foregoing general description and the following description are exemplary and explanatory only and are not restrictive of the methods and devices described herein. In this application, the use of the singular includes the plural unless specifically state otherwise. Also, the use of "or" means "and/or" unless stated otherwise. Similarly, "comprise," "comprises," "comprising," "include," "includes," "including," "has," "have," and "having" are not intended to be limiting.

Example embodiments are described herein in the context of medical devices and biocompatible constructs, and methods of making. Those of ordinary skill in the art will realize that the following description is illustrative only and is not intended to be in any way limiting. Other embodiments will readily suggest themselves to such skilled persons having the benefit of this disclosure. Reference will now be made in detail to various implementations of the example embodiments as illustrated in the accompanying drawings. The same reference indicators will be used to the extent possible throughout the drawings and the following description to refer to the same or like items.

Various embodiments of the devices and constructs of the present invention are also sometimes referred to as scaffolds, collagen scaffolds, membranes, implants and/or bio-devices. The terms biocompatible polymer and biopolymer are sometimes used interchangeably. The terms layer(s) and membrane(s) are sometimes used interchangeably.

Embodiments of the present invention describe methods to produce medical devices, constructs or implants comprised of compatible polymers for implantation or applied to various tissues to provide an anti-adhesion barrier and thus enhance repair and regeneration, among other uses. In some embodiments the biopolymer constructs are comprised of at least one layer or membrane of oriented collagen. In some embodiments the biopolymer constructs are comprised of multiple layers or membranes of oriented collagen. Of particular advantage, the multiple layers can be constructed with selected orientation to provide desired properties.

In another aspect, biopolymer constructs are provided comprised of at least one collagen layer and having a conductive element formed therein. In some embodiments the conductive element is one or more metal nanowires. Of particular advantage the conductivity of such devices, materials or implants may be selectively controlled by inducing magnetic fields which can be detected and monitored.

As used herein the term "fibrillar nanoweave biopolymer membrane" or simply "nanoweave membrane" means a fibrillar biopolymer membrane or layer where the filling fibrils or fibril bundles pass under and over alternate warp fibrils or fibril bundles, and the typical fibrils or fibril bundles have a helical or crimp shape in the unloaded state. Examples of various fibrillar nanoweave collagen membranes are shown in FIGS. 1A-1D. Specifically, FIGS. 1A-1D show four different nanoweave collagen membranes reconstituted from purified monomeric collagen solution in accordance with U.S. patent application Ser. Nos. 11/951,324, 11/986,263, 12/106,214, and 12/539,563 and used in embodiments of the present disclosure. The membranes or layers in FIG. 1A and FIG. 1B consist of aligned and aligned-braided helical collagen fibrils. In addition to a parallel alignment, the fibrils of the membrane in FIG. 1B form a crimp pattern of "ridges" aligned perpendicular to the fibril direction. The membrane shown in FIG. 1C consists of bundles (domains) of aligned collagen fibrils woven together. The collagen membrane of FIG. 1D has a "blood-vessel scaffold" structure of basket-weave collagen fibrils according to U.S. patent application Ser. Nos. 12/106,214, and 12/539,563 and can be used in some embodiments of the present disclosure;

The diameter of fibrils can be of any suitable size. In some embodiments, the diameter of the fibrils are in a range of 20 nm to 500 nm, depending on the tissue requirement. Methods of making these highly organized fibrillar biopolymer membranes or layers are described in U.S. patent application Ser. Nos. 11/951,324, 11/986,263, 12/106,214, and 12/539,563, the disclosures of all of which are incorporated by reference herein in their entirety.

One aspect of the present disclosure relates to devices and methods for preventing post-surgical or post-traumatic adhesion between wounded tissue and adjacent tissues, thus reducing scar and adhesion formation. In one example a method is provided comprising the steps of covering the wounded tissue and separating the wounded tissue from other surrounding tissues with a biopolymer based multi-layer construct which guides repair.

In some embodiments the biopolymer constructs are multi-layered. Multi-layered constructs may be made from fibrillar nanoweave biopolymer membranes or layers which may exhibit different structural characteristics, such structural characteristics being selected in order to promote regeneration in the wounded tissue and block further cell migration in the direction of surrounding tissues. For example, the construct may be formed by several cross-linked collagen layers configured such that in the vicinity of the wounded tissue one or more of the collagen layers have selected porosity and mechanical properties that promote repair and regeneration, while the outer collagen layers (or collagen layers remote from the wounded tissue) are designed to ensure the mechanical strength of the whole construct. Additionally, one or more of the outer collagen layers may exhibit selected properties that promote suturability of the construct, and/or provide a water-tight covering to prevent cell migration though the construct during the time required for the wound to repair and regenerate. Example of the nanoweave collagen layers with different porosity are illustrated in FIGS. 2A and 2B, which show AFM images of two different nanoweave collagen membranes reconstituted from purified monomeric collagen solution and having different porosity. The membrane shown in FIG. 2A has a woven skin-like structure with high porosity. In some embodiments this high porosity membrane has a pore diameter in the range 10-500 micrometers that permit repair cells to infiltrate said layer. In contrast, the membrane shown in FIG. 2B has skin-like structure with no or low porosity at the microscopic level (i.e. low porosity or water-tight). In some embodiments this low porosity membrane is water tight. In other embodiments this low porosity membrane is comprised of fibrillar nanoweave biopolymer layer pores having a diameter of equal to or lesser than 0.5 micron.

In some embodiments a fibrillar nanoweave layer has uniaxial or unidirectional orientation of the fibrils (e.g., tendon-like or cornea-like membrane). In some cases a fibrillar nanoweave layer has biaxial orientation of the fibrils (e.g., basket-weave membrane) over all, or a portion of, the layer. Additionally, the fibrillar nanoweave layer can exhibit a skin-like multi domain fibril orientation over all, or a portion of, the layer.

Different forms or collagen may be used. In some embodiments, monomeric collagen is used. One example of monomeric collagen is monomeric collagen I with cleaved telopeptydes or atellocollagen which has extremely low immunogenicity.

It is understood that fibrillar nanoweave collagen layer may influence non-scarring cell phenotype via mechanotransduction.

Biopolymer constructs according to the present disclosure are preferably biocompatible, mechanically stable, elastic, drapable, and suturable. In some embodiments, the construct or portion of the construct include a porosity gradient to provide enhance healing in the wound area and to promote a temporary barrier against uncontrolled distribution of blood, fibrinogen, necrotic material and damaged tissues.

Referring to FIG. 3, one embodiment of a multiplayer construct is shown. In this illustrative example, the construct 100 is generally comprised of top and bottom porous biopolymer layers 101, with water-tight biopolymer layers 102 formed therebetween, and an adhesive layer 103 formed between the water-tight layers 102. A planar network of nanowires 104 may be disposed in or on top of any of the layers. In the illustrative example, the planar network of nanowires 104 is disposed within one of the water tight layers 102.

Of particular advantage, the composition and/or structure of the various layers that comprise the construct may be specifically selected to provide certain desired properties and/or function. In one example, layers 101 are comprised of a porous membrane or layer similar to that shown in FIG. 2A; and layers 102 are comprised of a low porosity or water-tight membrane or layer similar to that shown in FIG. 2B. The adhesive layer 103 can be comprised of any suitable material. In one example—low molecular weight multi-arm activated polyethylene glycol (PEG), such as that commercially available at http://www.peg-drug.com/peg_product/branched.html can be used as the adhesive layer 103 between the two water-tight collagen membranes 102. UV exposure may be applied to covalently attach the two sheets.

Nanowires may be disposed within or on one of more of the layers in the construct. Suitable nanowires include, for example, metal nanowires, silver nanowires, piezoelectric nanowires, high density plastic nanowires, and combinations thereof.

In another embodiment the biopolymer construct comprises two multilayer sub-constructs wherein each sub-construct is configured with a different porosity gradient such that one sub-construct will degrade at a higher rate than the other sub-construct. Referring again to FIG. 3, a construct is provided such that each sub-construct 105a, 105b has a gradient porosity along the multilayer thickness, and the water-tight layers 102 of the two sub-constructs are attached by an adhesive layer 103 with a higher degradation rate than the water-tight layers 102 of the sub-constructs. Over time, defined separation between the two sub-constructs 105a, 105b will happen first as a result of degradation of the adhesive layer 103 which will leave a non adherent interface (not shown) between the two sub-constructs 105a, 105b. Degradation of the water-tight layers 103 will follow wound repair and regeneration. The sub-constructs act as hemostatic agent and inhibit uncontrolled fibrin deposition and distribution as well as hematomas, which are one of the main causes for fibrosis and adhesion formation.

Figure 4:
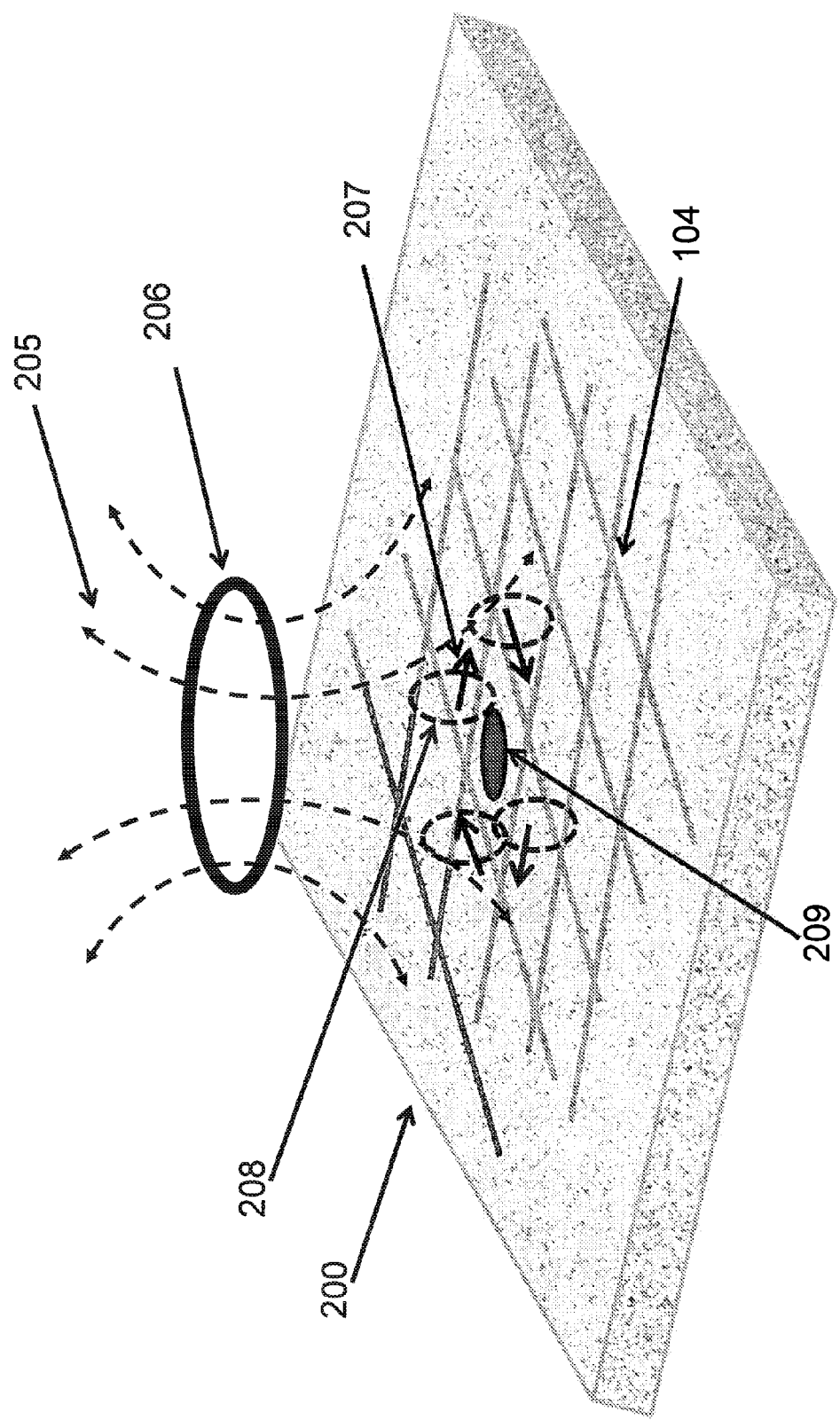
FIG. 4 is a schematic diagram of a device or construct that enable non-contact, non-invasive electromagnetic monitoring of adhesion formation in vivo according to some embodiments of the present disclosure.

Referring to FIG. 4, a biopolymer construct 200 containing a planar network 104 of metal nanowires is shown. Construct 200 enables non-contact, non-invasive electromagnetic monitoring of adhesion formation in vivo according to some embodiments of the present disclosure. In this illustrative example, construct 200 is generally comprised of one or more water-tight biopolymer layers, and a planar network of nanowires 204 which may be impregnated into the water-tight biopolymer layer. Of particular advantage, this construct is useful for one of more of preventing infection, enhancing repair and regeneration process, or reducing pain by pulse electromagnetic field (PEMF) stimulation. To induce a magnetic excitation field 205, an excitation coil 206 is applied which creates Eddy currents 207 and magnetic perturbation fields 208 around an adhesion spot 209. Sufficient electric current in the network inhibits excessive fibrin deposition and reduces inflammation by increasing production of nitric oxide, among other mechanisms.

When the biopolymer construct contains a planar network of nanowires, in situ monitoring the location of the construct using non-invasive magnetic induction spectroscopy (MIS) or other means is enabled. MIS requires an alternating magnetic excitation field which is coupled from an excitation coil to the object under investigation as shown in FIG. 4. Changes of the complex conductivity and changes of the relative magnetic permeability in the region of the planar nanowire network 104 cause a field perturbation 208 due to the induction of Eddy currents 207 and magnetic dipoles between the network cells. The perturbation field 208 is then measured via suitable receiver coils. Thus, a non-contact, non-invasive monitoring method of repair and regeneration process is disclosed. Suitable nanowires are, for example, comprised of silver nanowires or piezoelectric nanowires or combinations thereof.

The presence of piezoelectric nanowires in the planar network of metal nanowires imbedded in a multilayer construct turns the multilayer construct into a smart device. The mechanical deformation caused by cell adhesion and migration excites electric current in the piezoelectric nanowires, which generate a magnetic field detected by receiving coil. In response, the excitation coil generates a magnetic field which causes an electric field in metal nanowires to release a suitable drug and/or stop cell proliferation.

Of significant advantage, in another embodiment deformation of the nanowire network under different mammal body positions may be used as an indication of post surgical or post-traumatic adhesion. The deformation can be measured, for example, by x-ray stereotactic device. Suitable nanowires in this embodiment are, for example, comprised of high density plastic nanowires or metal nanowires.

In one example of the present disclosure the construct preventing cell adhesion by the method according to the present disclosure can be applied to medical or veterinarian uses.

Methods disclosed herein of covering and separating tissue with a multilayer construct may be carried out during the treatment of any injuries or defects, for example, the dura mater covering the brain or the spinal column. In one example of the present disclosure, the step of covering and separating the tissue with a multilayer construct may be carried out during abdominal surgery.

FIGS. 5A-5C are an illustration showing an exemplary method of preparing a multilayer construct according to embodiments of the present disclosure. In some embodiments, a nanoweave collagen membrane or layer 510 is deposited on a surface and then is peeled off from substrate 511 as shown in FIG. 5A. If desired, multiple membranes or layers 510 may be laminated in a cross wise fashion (cross-lamination) as shown in FIG. 5B.

EXPERIMENTAL

A number of experiments were conducted as described below. These examples are shown for illustration purposes only and are not intended to limit the invention in any way.

Example 1: Preparation of Multilayer Biocompatible Construct/Implant

Multiplayer constructs were prepared by the following method: liquid fibrillar biopolymer (e.g. purified medical grade collagen to substrate (glass or plastic, e.g. PET film)) was deposited to form a solid film (matrix) according to the procedure described in the patent applications: WO2010/019625A2, US2009/0069893A1, WO/2008/070166A1, WO/2008/063631A2. The typical film thickness is in the range from 1 μm to 10 μm.

The film was removed from the substrate in the direction of the collagen fibrils (deposition direction, see FIG. 5A). The deposited film has sufficient strength in the fibril direction.

The multiple collagen films were Cross-laminated as shown in FIG. 5B. The bonding material and/or additional material or drug can be sprayed or otherwise applied between collagen layers (films), e.g. heparin or glutaraldehyde or genipin or other cross-linking materials can be deposited between layers.

The resulting multilayer construct can be placed into dehydration unit (e.g., vacuum of at least 50 millitorr and temperature 90° C. for 72 hours).

The construct should be further sterilized (e.g. E-beam sterilization) and it is ready for use for biomedical applications.

Example 2: Preparation of Multilayer Construct/Implant

In this experiment, multilayer constructs were prepared by depositing the liquid biopolymer (e.g. collagen) to substrate (glass or plastic, e.g. PET film) to form a solid film (matrix) according to the procedure described in the patent applications: WO2010/019625A2, US2009/0069893A1, WO/2008/070166A1, WO/2008/063631 A2. The typical film thickness is in the range from 1 μm to 10 μm.

The coated film is attached to a carrier (e.g., to a transparent flexible film with double-sided tape area at the film perimeter or a drum with vacuum/electrostatic holder) and removing the substrate as shown in FIG. 5C).

The multiple fibrillar films are transferred and laminated on a non-adhering substrate. The bonding material and additional materials including bioactive material can be sprayed or deposited between fibrillar layers (films), e.g. heparin, multi-arm activated PEG, metal or plastic nanowires can be deposited between layers.

The resulting multilayer construct can be placed into dehydration unit (e.g., vacuum of at least 50 millitorr and temperature 110° C. for 72 hours under pressure).

The construct should be further sterilized (e.g. E-beam sterilization).

In the two examples above the lamination process is conducted in a way to avoid wrinkles or bubbles. One modification of the above procedure (step 0053) includes a spray of microparticles (e.g. low molecular weight PEG particles of 40 micron diameter) together with cross-linking droplets, such that the PEG can be dissolved after the cross-linking of the multilayer construct (at the step 0054). The purpose of this modification is to modify the porosity at the interface between layers and to control the strength of adhesion between the layers.

Figure 6A:
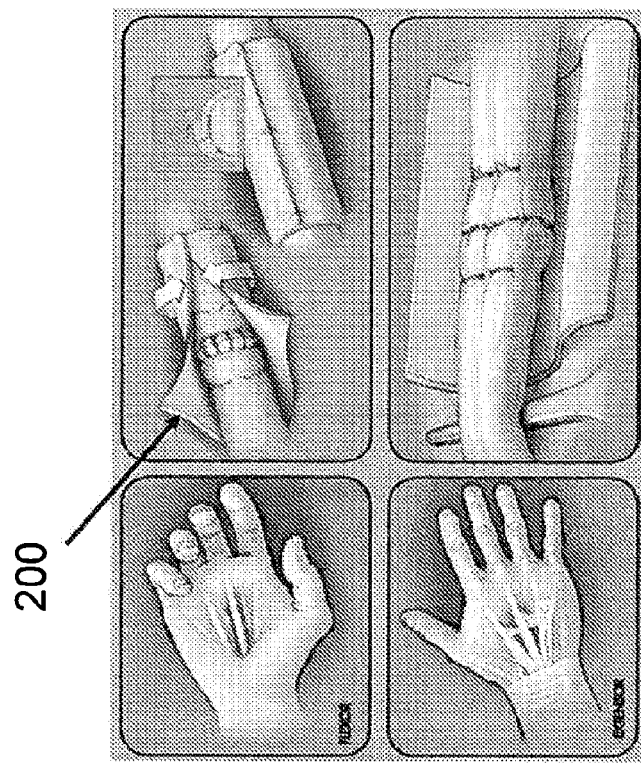
FIGS. 6A-6B are illustrations of two known prior art techniques for providing an adhesion barrier, a dural barrier and tendon sheath, respectively.
Figure 6B:
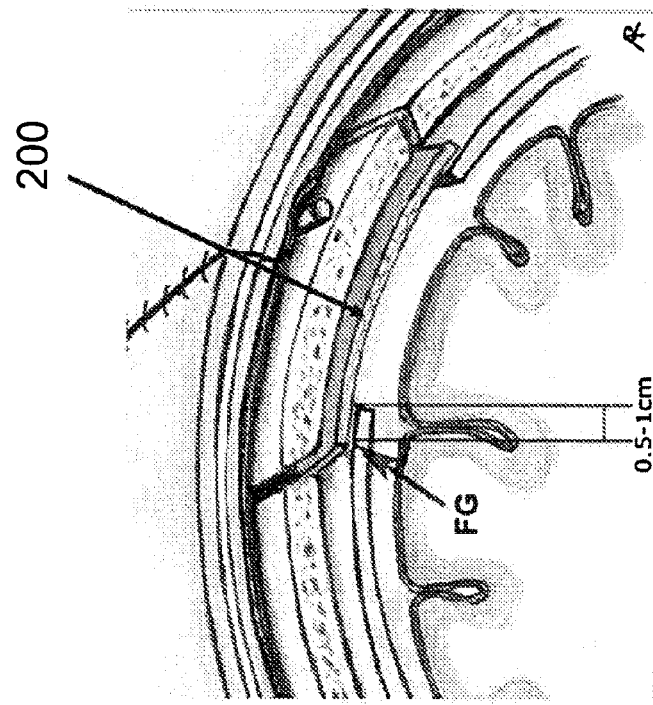

In addition to being used as an anti-adhesion barrier during or after surgery, the multilayer construct/implant can be used as or with a tendon sheath or a dural barrier as shown in FIGS. 6A-6B.

Various laminated constructs can be made from the medical grade monomeric collagen solution by methods described above. The constructs may be formed of any number of layers. In one example, and without limitation, a construct with twelve cross-laminated layers is provided having six (6) layers with aligned fibrils in one direction and six (6) layers with aligned fibrils in an orthogonal direction. In one experiment such a twelve layer construct was formed and having weight of the sample in the dry state of 14 mg, size of 25×25×0.02 mm, and density of 1.12 mg/mm$^3$. A sample with two cross-laminated layers was formed having weight is in the dry state of 2 mg, size of 25×25×0.0025 mm, and a density of 1.28 mg/mm$^3$. Both samples are transparent in dry and wet state with transmittance at 630 nm more than 70% and about 90% respectively. The diffraction patterns of both samples were measured and are shown in FIG. 7A. To measure the diffraction patterns, an experimental setup was constructed having a screen 714 and a red laser 715. The laser light passes through the multilayer construct 200 and produces a diffraction pattern on the screen 714. Photo 716 is the diffraction patent of the multilayer construct. FIG. 7B shows diffraction patterns of the nanoweave membranes according to the present disclosure as shown in FIG. 1A and FIG. 1B, respectively. As shown, both samples have distinctive diffraction patterns, which is representative of their highly ordered orientation. The distance from construct to the screen is 30 cm. This pattern is the composition of the patterns from the single layer shown at FIG. 7B. It is typical for the tendon-like nanoweave membrane (e.g., see FIG. 1B) and corresponds to the parallel ridges (crimped fibrilar structures) well described in WO2010/019625A2 and US2009/0069893A1.

The typical collagen matrices on the market have low density and isotropic scattering/diffraction pattern. For example, typical dental collagen membrane has weight in the dry state—65 mg, size 20×30×0.1 mm, and density 1.08 mg/mm$^3$. FIG. 7C illustrates a diffraction patterns of a typical collagen membrane on the market showing no orientation to the material. It is translucent in a wet state and has isotropic scattering pattern as shown in FIG. 7C which indicates randomly oriented fibrils.

Example 3: Multilayer Construct with Planar Network of Silver Nanowires

Figures 8A, 8B:
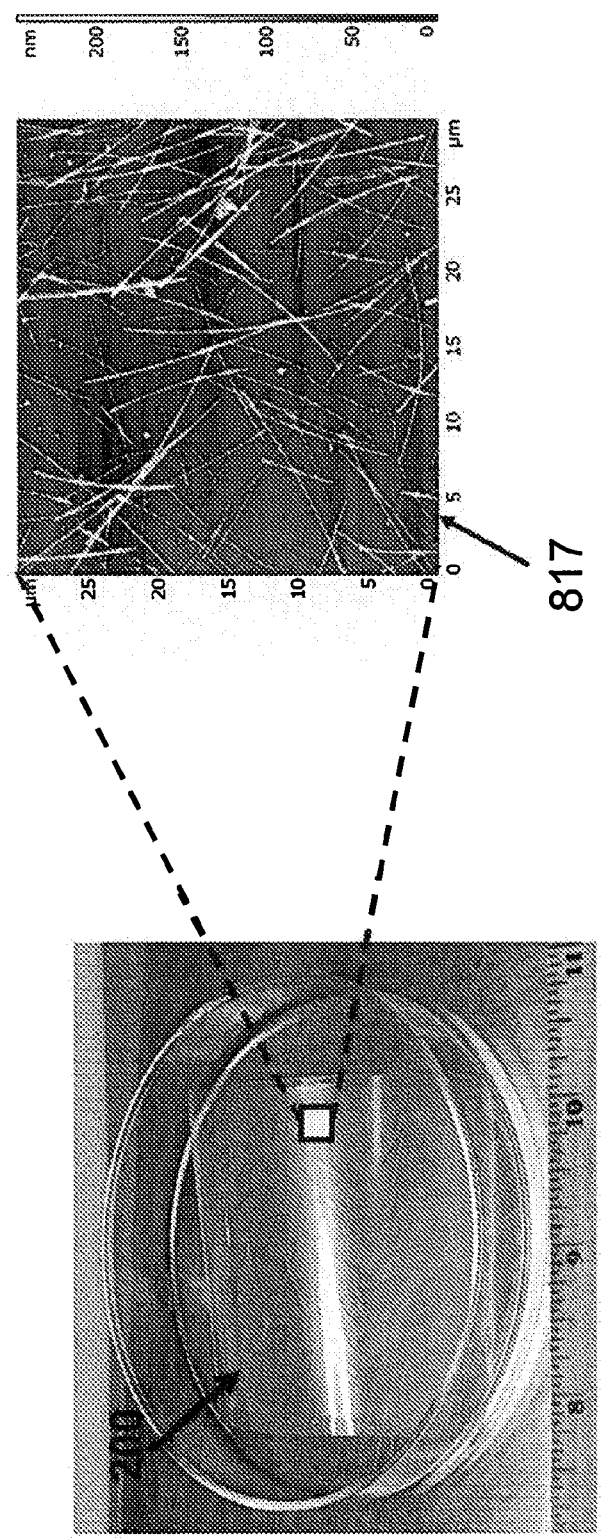
FIGS. 8A-8B show a construct comprised of twelve transparent collagen layers made by the method described in Example 2; and having planar silver nanowire network at the interface between two nanoweave transparent layers.

A multilayer construct comprising a planar network of silver nanowires was prepared according to the procedure described in Example 1. An aqueous silver nanowire solution 2 wt % (SeaShell Technology, San Diego) was deposited between two laminated fibrillar collagen nanoweave membranes as shown in FIG. 8A. After water evaporation, silver nanowires form a connected network 817 as shown in FIG. 8B. The multilayer construct 200 at the FIG. 8A has been further crosslinked and sterilized in 70% ethanol. The typical diameter of the silver nanowire is 50 nm with the average length of about 10 microns therefore the network has good contrast in MIS.

Example 4: Use of Multilayer Construct Prepared According to Procedure Described in the Example 1 as an Adhesion Barrier in Animal Study Four types of multilayer collagen constructs are used in this experiment: constructs without additional treatment; constructs which have one side treated by activated PEG; constructs which have one side treated by heparin; and constructs which have one side treated by activated PEG and albumin such that albumin forms an external monolayer.

The goal of this experiment was to test the ease of handling of the multilayer constructs; and to test whether surface-modified multilayer constructs prevent formation of adhesions.

Experimental design: After induction of anesthesia, perform an adhesion induction by brushing the secum and peritoneal wall by a Perlon brush (tooth brush). In experimental animals, wrap the traumatized secum with multilayer collagen construct such that the treated surface of the construct faces peritoneal wall. In control animals, no wrapping is performed. Sacrifice in 12 days to check for adhesion formation.

Animals: Balb/c, female, DOB 4/26, 20 g; CD1, male, DOB 2/27, 40-42 g.

Experimental groups: A—control group (no wrap)—3 animals; B—collagen construct without treatment—3 animals; C—collagen construct treated by activated PEG—3 animals; D—collagen construct treated by heparin—3 animals; E—collagen construct treated by activated PEG and albumin—3 animals.

Anesthesia. Animals were anesthetized with isoflurane following 100 mg/kg ketamine and 5 mg/kg body weight xylazine.

Animal preparation. Animals were shaved on the abdominal side and the residual hair were removed with hair removal cream (diluted 1:1 w/H2O) application for 3 min. The site of the incision was disinfected with chlorhexidine gluconate.

Adhesion induction. Mice were placed in a supine position and the abdomen was exposed through a ventral midline incision. Standardized surgical injuries were applied to visceral and parietal peritoneum and the secum: a 1×1-cm area of the left sidewall peritoneum was brushed with a Perlon brush until punctuate bleeding occurred. The same trauma was applied to the secum. The animals were then randomized to their groups and treated accordingly. The collagen constructs were used to wrap the traumatized secum, so that it would form a barrier between the secum and the peritoneal wall. After traumatization, the abdomen was closed with Vetbond tissue adhesive. The skin was closed with easy-clips.

Post-surgery management. All animals were administered with antibiotic (cefazolin, 15 mg/kg, s.c., day 0 and 1) and analgetic (Buprenex (buprenorphine hydrochloride), 2 mg/kg, s.c., days 0 and 1).

The best results with minimum adhesion were observed for the group E; the worst results with multiple adhesions were occurred in the group D. In all groups the multilayer constructs have shown excellent drapability and good mechanical strength.

Example 5: In-Vitro Model of Vascular System

Cells can be analyzed in a variety of models, such as in a blood vessel model, or cornea model, and the like (see, e.g., FIG. 9A-9C). FIGS. 9A-9C are a series of photographs and drawing illustrating the use of a multilayer collagen construct (FIG. 9B) with orthogonal orientation of fibrils. As shown in FIG. 9C, two different cell types are plated on the top and bottom sides of the construct (e.g., epithelial and endothelial cells in the case of corneal in-vitro model or smooth muscle and endothelial cells in the case of blood vessel in-vitro model). The construct with the attached cells can be further transferred into specific animal site (e.g., to a wound or to another in-vitro system as shown at the FIG. 9A.).

Embodiments of the present disclosure provide in-vitro modeling. Advantages of the present invention include: an option to use high transparency membrane; control the tension on the frame; control of rigidity and/or the structure of the nanoweave membrane. Referring again to FIG. 9A, the frame has two parts: top frame and bottom frame such that they can keep the membrane between them with a desired tension. The frame also may have the sensors to measure the stress induced by the cells. The control rigidity can be achieved by forming PDMS-type layer as a part of the laminate. For some applications it is important to have good adhesion between PDMS and the collagen layer. It can be achieved by pouring a desirable composition of PDMS-type material on the collagen (fibrillar biopolymer) membrane and polymerizing the composition together in dehydration unite (e.g., vacuum of at least 50 millitorr and temperature 80° C. for 24 hours). Example of the double layer collagen membrane is shown in FIG. 9B. The top layer membrane is plated by smooth muscle cells; the bottom layer is plated by endothelial cell. As one can see in FIG. 9C the cells are aligned in the orthogonal direction along the collagen fibrils. It is the model of blood vessel.

Additional application for the multilayer constructs include, without limitation: cell culture research applications, cell/drug delivery applications, and other tissue engineering applications.

In vitro assays using multilayer constructs of the present disclosure include, without limitation: stem cell attachment, proliferation on collagens 1, 4 or laminin, or fibronectin; factors inducing stem cell proliferation; quantitative stem cell migration assays/required factors; neurite formation in cells derived from neural stem cells; myoblast/cardiomyocyte differentiation and function; tubule formation by kidney derived and other cells; differentiation of IPS cells along epithelial or neuronal lines; co-culture of islets with stem cells.

In vivo assays using multilayer constructs of the present disclosure include, without limitation: multilayer constructs for stem cell/islet transplantation; sheets for transplantation of bioluminescent cells to certain sites for tracking their migration and survival; sheets for transplantation of tumor cells in vivo to specific sites; transparent constructs to facilitate imaging of implanted stem cells; device for growing stem cells in culture and transferring them to specific tissue sites; implantable biocompatible collagen/silver nanowire constructs to enhance the proliferation, differentiation and vascularization of implanted stem cells using PEMF signals.

Tissue damage to heart, striated muscle, skin, bone and cartilage, tendon and ligament, spinal cord and the like often progresses and causes the breakdown of normal surrounding tissue increasing the area of damage and seriously impairing tissue function. Current concepts suggest that various factors or cells could be introduced into the damaged area by direct injection and prevent further damage and even cause regeneration of the damaged area. Indeed, preclinical as well as clinical trials have shown improved heart function when mesenchymal stem cells are injected into the site of tissue damage. However, such studies have also shown that significant amounts of the injected cells leak out of the tissue and most of the cells remaining rapidly die. Thus there are uses for devices which allow delivery of various types of cells to specific sites in damaged tissue and maintain their survival and expansion. However, the physical properties of different tissues vary strikingly (compare heart muscle with striated muscle with skin or spinal cord). Thus, delivery vehicles should have sufficient strength to allow them to be placed in a specific tissue without causing alterations in tissue function due to poorly matched physical factors. This calls for materials whose physical properties are suitable for the tissue in which they are to be used. Also, cells require factors and surfaces to support their survival, migration and production of specific repair factors. In brief, the treatment of damaged tissues should be improved by novel devices which would deliver and maintain stem and other cells in specific sites to allow them to survive and produce factors that sustain tissue at risk.

Multilayer constructs of the present disclosure provide cell guiding and can be used for repair and regeneration of periodontal ligament. Top layer of the construct may have the fibril orientation which blocks a migration of gingival epithelial cells to the tooth. The bottom layer has the collagen fibrils orientation which promotes repair and regeneration of the periodontal ligament (vertical fibrils). Collagen-based construct can be used effectively for a wound treatment. They can be supplemented with small molecules, peptides, PRP (platelet reach plasma), stem cells, vanadate, etc. These examples are not limiting the applications of the above constructs.

The foregoing methods, materials, constructs and description are intended to be illustrative. In view of the teachings provided herein, other approaches will be evident to those of skill in the relevant art, and such approaches are intended to fall within the scope of the present invention.

We claim:

1. An implantable multilayer construct promoting repair and regeneration of a wounded or defective tissue, preventing an adhesion to surrounding tissue, and preventing excessive fibrotic reaction of the injured tissue and comprising: at least two fibrillar nanoweave biopolymer layers attached by intermediate biodegradable layer where the intermediate layer has a rate of degradation higher than at least one nanoweave biopolymer layer under physiological conditions.

2. The multilayer construct according to claim 1, wherein the at least two fibrillar nanoweave biopolymer layers enables cell guidance and tissue regeneration.

3. The multilayer construct according to claim 1 wherein the at least two fibrillar nanoweave biopolymer layers stimulates non-scarring phenotype for adherent cells.

4. The multilayer construct according to claim 1 wherein the at least two fibrillar nanoweave biopolymer layers is made from collagen.

5. The multilayer construct according to claim 1 wherein the at least two fibrillar nanoweave biopolymer layers is comprised of oriented fibrillar biopolymer material.

6. The multilayer construct according to claim 1 wherein one of the fibrillar nanoweave biopolymer layers has no pores with diameter greater than 0.5 micron.

7. The multilayer construct according to claim 1 or claim 6 further comprising a biopolymer layer with the pore diameter in a range 10-500 micrometers that permit repair cells to infiltrate said layer.

8. The multilayer construct according to claim 1 wherein the intermediate layer has a gradient degradation rate with slow degradation at the surface of fibrillar nanoweave biopolymer layers and the highest degradation in the median plane between nanoweave biopolymer layers such that the degradation is separating multilayer construct to at least two parts with low friction and low tissue adhesion between them.

9. The multilayer construct according to claim 1 where the intermediate layer comprises a biologically active agent being arranged to be released by the construct through a period of desired duration.

10. The multilayer construct according to claim 9 wherein the biologically active agent is effective in preventing tissue adhesions.

11. The multilayer construct according to claim 1 which has diffusive transmittance in the visible spectrum more than 20%.

12. The multilayer construct according to claim 1 further comprising at least one planar network of nanowires.

13. The multilayer construct according to claim 12 where the nanowires selected from one or more of: metal nanowires, or plastic nanowires, or piezoelectric nanowires, or the combination thereof.

14. The multilayer construct according to claim 12 wherein the nanowires form a planar array of cells or coils.

15. The multilayer construct according to the claim 12 or claim 14 where an external alternating magnetic excitation field applied to the construct after implantation of the construct into a mammal body is coupled to the planar nanowire network to monitor changes of the complex conductivity and changes of the relative magnetic permeability in the region of the planar nanowire network by suitable external receiver coils measuring a field perturbation due to the induction of Eddy currents and magnetic dipoles between the network cells.

16. The multilayer construct according to claim 12 where, after implantation of the construct into a mammal body, the network deformation under different mammal body positions is measured by a suitable x-ray stereotactic device and used to estimate post surgical or post-traumatic adhesion.

17. The multilayer construct according to claim 12 wherein an external alternating magnetic excitation field applied to the construct after implantation of the construct into a mammal body is coupled to the planar nanowire network to enhance tissue repair and regeneration and to reduce pain.

18. The multilayer construct according to claim 1 where intermediate biodegradable layer comprises electrically conductive layer.

19. The multilayer construct according to claim 1 or claim 18 further comprising: conductive layer serving as biocompatible biodegradable antibacterial electrode and scaffold for neuromuscular electromagnetic stimulation, electromagnetic stimulation for tissue repair, pain management with electromagnetic stimulation, and for transdermal drug delivery.

20. The multilayer construct according to the claim 18 wherein the electrically conductive layer triggers and controls the separation under external pulsed electromagnetic field.

21. The multilayer construct according to claim 1 which has at least one layer comprising hyaluronic acid, chondroitin 6-sulphate, keratin sulphate, dermatan sulphate, PEG, laminin, albumin, alginate, heparin, polyacrylic acids, polymethacrylic acid, polyethylene amine, polysaccharides, alginic acid, pectinic acids, carboxy methyl cellulose, chitosan, carboxymethyl chitosan, carboxymethyl starch, carboxymethyl dextran, heparin sulfate.

22. The multilayer construct according to claim 1 which has one surface promoting adhesion to tissue and the other surface inhibits adhesion to tissue under physiological conditions and act as a barrier to prevent passage of cells there through.

23. A multilayer construct according to claim 1 promoting repair and regeneration of a damaged or wounded area of patient's spinal cord and preventing an adhesion to surrounding tissue and excessive fibrotic reaction of the injured tissue.

24. The multilayer construct according to the claim 1 further comprising at least one layer which has laser diffraction pattern with at least one elongated branch.

\* \* \* \* \*